US007076435B1

(12) United States Patent
McKeag et al.

(10) Patent No.: US 7,076,435 B1
(45) Date of Patent: Jul. 11, 2006

(54) METHOD FOR TRANSFERRING PATIENT INFORMATION FROM A SOURCE MONITOR TO A DESTINATION MONITOR

(75) Inventors: Gregory A. McKeag, Duvall, WA (US); Kenneth S. Wade, Woodinville, WA (US); David P. Finch, Bothell, WA (US)

(73) Assignee: Datex-Ohmeda, Inc., Madison, WI (US)

( * ) Notice: Subject to any disclaimer, the term of this patent is extended or adjusted under 35 U.S.C. 154(b) by 0 days.

(21) Appl. No.: 08/247,024

(22) Filed: May 20, 1994

Related U.S. Application Data

(62) Division of application No. 08/052,132, filed on Apr. 22, 1993, now abandoned.

(51) Int. Cl.
*A61B 5/00* (2006.01)
(52) U.S. Cl. .......................... 705/3; 600/300; 707/102
(58) Field of Classification Search ........... 364/413.02, 364/413.01, 413.03; 128/710; 705/2, 3; 600/300; 707/102
See application file for complete search history.

(56) References Cited

U.S. PATENT DOCUMENTS

| | | | | |
|---|---|---|---|---|
| 4,356,475 A | * | 10/1982 | Neumann et al. ........... 340/521 |
| 4,378,021 A | * | 3/1983 | Strand ......................... 128/709 |
| 4,688,579 A | * | 8/1987 | Inahara .................... 128/695 R |
| 4,779,199 A | * | 10/1988 | Yoneda et al. ......... 364/413.03 |
| 4,784,162 A | * | 11/1988 | Ricks et al. ................. 128/903 |
| 4,803,625 A | * | 2/1989 | Fu et al. ................. 364/413.03 |
| 4,835,372 A | * | 5/1989 | Gombrich et al. ........... 235/375 |
| 4,895,161 A | * | 1/1990 | Cudahy et al. ............. 128/710 |
| 4,916,441 A | * | 4/1990 | Gombrich .................... 345/169 |
| 5,012,411 A | * | 4/1991 | Policastro et al. ...... 364/413.06 |
| 5,024,225 A | * | 6/1991 | Fang ........................... 128/630 |
| 5,029,590 A | * | 7/1991 | Allain et al. ................. 128/710 |

(Continued)

FOREIGN PATENT DOCUMENTS

JP 02140151 A * 5/1990

OTHER PUBLICATIONS

PDMS, "What the PDMS Does an Overview" pp. ii-1 thru 2-23.*

(Continued)

*Primary Examiner*—Joseph Thomas
*Assistant Examiner*—R. L. Porter
(74) *Attorney, Agent, or Firm*—Dorsey & Whitney, LLP

(57) ABSTRACT

A method and system for transferring patient information from a source patient monitor having a source patient database to a destination patient monitor having a destination patient database. In a preferred embodiment, a transport module is connectable to a source patient monitor and a destination patient monitor. The transport module is also connectable to a patient for receiving patient information. The transport module contains a transport database for storing patient information. The transport module is connected to the patient. The transport module is then connected to the source patient monitor. Upon receiving a request to move the patient, patient information is uploaded from the source patient database to the transport database. The transport module is then disconnected from the source patient monitor. The patient is then moved. The transport module is then connected to the destination patient monitor and patient information is downloaded from the transport database to the destination patient database. In a preferred embodiment, the uploading and downloading of patient information occur concurrently with read/write access to the destination and source patient databases by a central monitor or data collection module.

13 Claims, 5 Drawing Sheets

U.S. PATENT DOCUMENTS

| | | | |
|---|---|---|---|
| 5,036,856 A | * | 8/1991 | Thornton .................... 128/670 |
| 5,226,431 A | * | 7/1993 | Bible et al. ................. 128/904 |
| 5,228,450 A | * | 7/1993 | Sellers ....................... 128/711 |
| 5,239,997 A | * | 8/1993 | Guarino et al. ............. 128/630 |
| 5,267,147 A | * | 11/1993 | Harshaw et al. ............ 364/401 |
| 5,307,263 A | * | 4/1994 | Brown ................. 364/413.09 |
| 5,375,604 A | * | 12/1994 | Kelly et al. ................. 128/671 |

OTHER PUBLICATIONS

"Unity Monitoring Network" brochure by Marquette Electronics, Inc., copyrighted 1990.*

* cited by examiner

METHOD FOR TRANSFERRING PATIENT INFORMATION FROM A SOURCE MONITOR TO A DESTINATION MONITOR

CROSS-REFERENCE TO RELATED APPLICATION

This application is a division of U.S. patent application Ser. No. 08/052,132, filed Apr. 22, 1993 now abandoned.

TECHNICAL FIELD

This invention relates generally to a computer system for extracting information from a database and, more specifically, to a method and system of extracting time-dependent data from a database.

BACKGROUND OF THE INVENTION

In a hospital environment, patient monitors are commonly used to monitor a patient. A patient monitor is a computer system with various input sensors for collecting patient information, a database for saving the information, and a display for displaying the information to a health care provider. Patient information typically includes heart rate, blood pressure, electrocardiographic and electroencephalographic information. Patient information may also include patient descriptive information, such as, patient name, age, etc.

The information collected by the patient monitor is typically categorized as being general or periodic. General information includes patient descriptive information and episodic information. Episodic information are various measurements that are sampled on an ad hoc basis. For example, a health care provider may, from time to time, determine a patient's blood pressure and manually enter the blood pressure reading into the monitor. Periodic information includes various measurements of activity that are sampled continuously, such as, heart rate and electrocardiographic activity.

FIG. 1 is a block diagram illustrating a network of patient monitors in a typical hospital environment. The network comprises a central monitor computer system 101 connected to various patient monitors 102. The central monitor 101 is typically located at a nursing station and allows the activity of many patients to be monitored from the nursing station. The central monitor 101 comprises a central database 111, a controller program 112, and communications program 113. To collect patient information from the patient monitors 102, the controller program 112 instructs the communications program 113 to retrieve the patient information from the patient monitors 102. When the communications program 113 receives the information, it passes the information to the controller program 112. The controller program 112 stores the information in the central database 111. In response to a request to review the information, the controller program 112 retrieves data from the central database 111 and displays the data. The patient monitors 102 comprise a communications program 103, a controller program 104, a patient database 105, and a sensor interface program 106. The controller program 104 controls the collecting of patient information through sensor interface program 106 and the storing of the collected information in the patient database 105. When the communications program 103 receives a request to transmit information to the central monitor 101, the communications program 103 sends the request to the controller program 104, which retrieves the requested information from the patient database 105. The controller program 104 then sends the retrieved information to the communications program 103, which transmits the data to the central monitor 101.

FIG. 2 is a block diagram illustrating typical information stored in the patient database 105. Information in the patient database typically includes a current entry number 201, an audit log 202, a time history list 203, general information 204, and periodic information 205. Whenever information in the patient database is added, an entry number is stored with the added information. Current entry number 201 represents the entry number to be stored with the next added information. The entry number uniquely identifies each entry in the database. The audit log 202 is a table that contains a history of changes to the database. The time history list 203 is a table used to track clock changes in a patient monitor. These changes occur, for example, when someone notices that a clock on the patient monitor is off by ten minutes and then sets the clock ahead by ten minutes. An entry is stored in the time history list 203 indicating a change in time. The time history list allows a reconstruction of the sequence of events that have occurred. When reconstructed, a ten-minute apparent gap in the information would be interpreted not as a ten-minute gap, but rather as a continuous recording of patient information. The general information 204 is stored as a linked list of general information blocks 204A, 204B. Each general information block includes a header containing timing information of the data in the block and includes the general information. The periodic information 205 is stored in trend information blocks. Each trend information block comprises a trend structure 205A and trend stream 206A, 206B. Each trend information block holds information from one type of monitored patient activity (e.g., heart rate). Each trend stream 206A, 206B contains an entry for each measurement made by the patient monitor of the monitored activity. The trend structure 205A includes a pointer to the trend stream 206A, time of the last entry into the trend stream 206A, and various other trend-specific information.

In a hospital environment, patients who are connected to patient monitors are often transported throughout the hospital. For example, after surgery a patient is transported from the operating room to a recovery room. Typically, when a patient is transported, the patient is disconnected from the sensors that are connected to the patient monitor, transported to a new location, and then reconnected to the sensors that are connected to a patient monitor at the new location. Problems are, however, associated with transporting a patient in such a way. First, it can be time-consuming to disconnect and reconnect sensors. Second, the patient monitor at the new location typically cannot access the information that was collected by the patient monitor at the old location. This makes it difficult for a health care provider to track the history of a patient, especially when the patient monitors are not connected to a central monitor. To avoid these problems, the patient monitor can be transported with the patient being connected to the sensors. However, the transporting of patient monitors can be cumbersome and impractical because of their size. Also, various types of patient monitors may be needed that range from very expensive to relatively inexpensive. For example, a patient in an operating room may need extensive monitoring by an expensive patient monitor. It is not cost-effective to transport such an expensive operating room patient monitor to a recovery room and then to the patient's room. It would be more cost-effective to use a less sophisticated (and less expensive) patient monitor in the patient's room.

SUMMARY OF THE INVENTION

It is an object of the present invention to provide a method and system for transferring patient information from a source patient monitor to a destination patient monitor.

It is another object of the present invention to provide a method and system for uploading data from a source patient monitor to a transport module for transfer to a destination patient monitor.

It is another object of the present invention to provide a method and system for downloading data from a transport module to a destination patient monitor.

It is another object of the present invention to provide a method and system for uploading patient information from a patient database and downloading patient information to a patient database while allowing concurrent read/write access to the patient database for continuous patient monitoring.

These and other objects, which will become apparent as the invention is more fully described below, are obtained by a method and system for transferring patient information from a source patient monitor having a source patient database to a destination patient monitor having a destination patient database. In a preferred embodiment, a transport module is connectable to a source patient monitor and a destination patient monitor. The transport module is also connectable to a patient for receiving patient information. The transport module contains a transport database for storing patient information. The transport module is connected to the patient. The transport module is then connected to the source patient monitor. Upon receiving a request to move the patient, patient information is uploaded from the source patient database to the transport database. The transport module is then disconnected from the source patient monitor. The patient is then moved. The transport module is then connected to the destination patient monitor and patient information is downloaded from the transport database to the destination patient database.

DETAILED DESCRIPTION OF THE INVENTION

Figure 1:
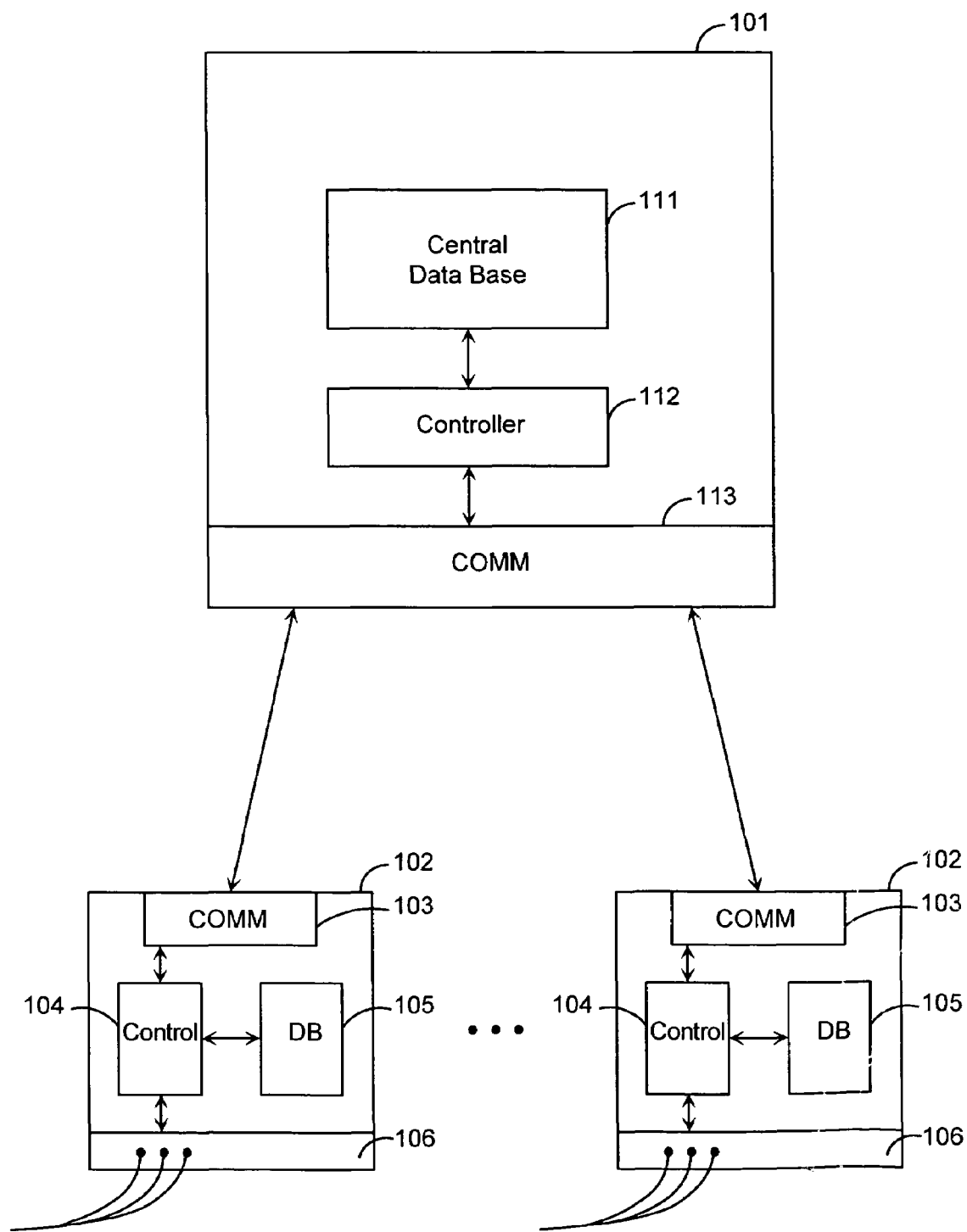
FIG. 1 is a block diagram illustrating a network of patient monitors in a typical hospital environment.
Figure 2:
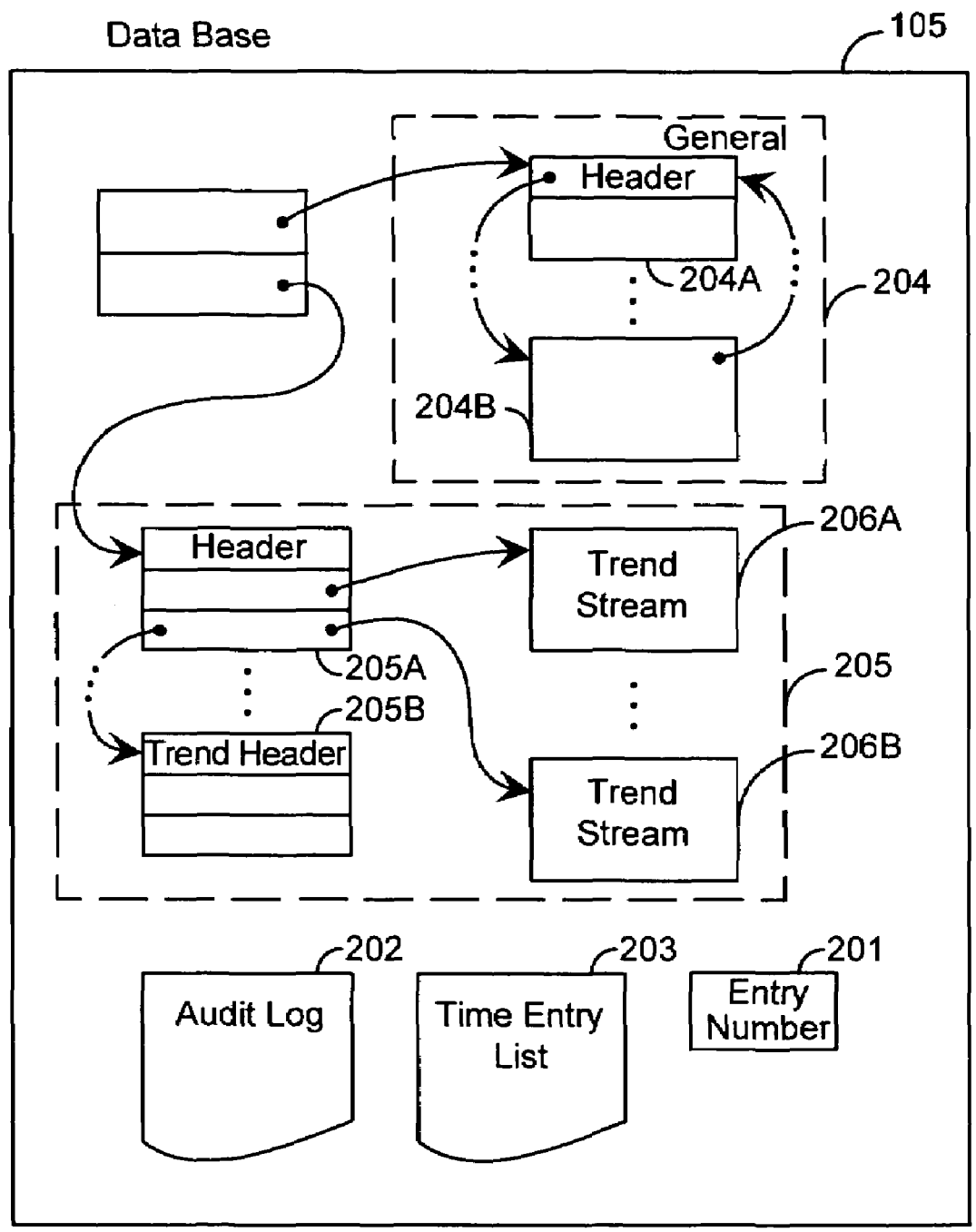
FIG. 2 is a block diagram illustrating typical information stored in the patient database 105.

In a preferred embodiment, the present invention provides a method and system for disconnecting a patient from a source patient monitor and reconnecting the patient to a destination patient monitor without disconnecting the patient from the sensors while providing the destination patient monitor with access to information collected at the source patient monitor. In a preferred embodiment, a source patient monitor is connected to a removable transport module. The transport module is a computer system that includes an interface to sensors, a memory for storing patient information during transport, a communications program for communicating with a patient monitor, and programs for uploading and downloading information from and to a patient monitor. A patient is initially connected to a source patient monitor through the transport module. The transport module controls the collecting of the patient information and forwarding of the information to the source patient monitor for storage in a patient database. When a patient is to be transported, a health care provider indicates to the source patient monitor that a transport is imminent. The source patient monitor then uploads the most current patient information to the transport module, which stores the patient information in its memory. When the upload is complete, the transport module, which is a portable device, is disconnected from the source patient monitor and transported along with the patient, who is still connected through the sensors through the transport module, to a destination location. At the destination location, the transport module is connected to a destination patient monitor. Either under control of the health care provider or automatically upon connection, the patient information stored in the memory of the transport module is downloaded to the patient database of the destination patient monitor. The destination patient monitor then has access to the most current patient information.

The present invention provides a method and system for extracting patient information from a source patient monitor. A preferred method allows patient information to be collected and allows patient information to be transmitted to a central monitor while an upload is in progress. In a preferred embodiment, the extraction system first transfers context information, describing the state of the patient database, to the transport module. Second, the extraction system transfers time-independent information (e.g., patient name) to the transport module. Third, the extraction system transfers information from the trend information blocks to the transport module. Typically, information is transferred to the transport module in a transfer buffer with a designated size.

The present invention provides an extraction system in which trend information from the various trend information blocks is transferred so that generally the most recent trend information is transferred first. The general information is considered to comprise trend data. In a preferred embodiment, patient descriptive data is stored as general information with a time in the future so that the patient descriptive information is the first transferred. The extraction system selects a first trend information block to transfer. The extraction system fills (as much as possible) the transfer buffer with trend information from the selected trend information block, transfers the transfer buffer to the transport module, and records the age of the trend information that is transferred. The extraction system then selects a trend information block with the most recent information that has not yet been transferred. The extraction system then fills the transfer buffer with trend information from the selected trend information block, transfers the transfer buffer to the transport module, and records the age of the trend information transferred. The extraction system then repeats this process until either the transport module is full or all the patient information is transferred.

Figure 3:
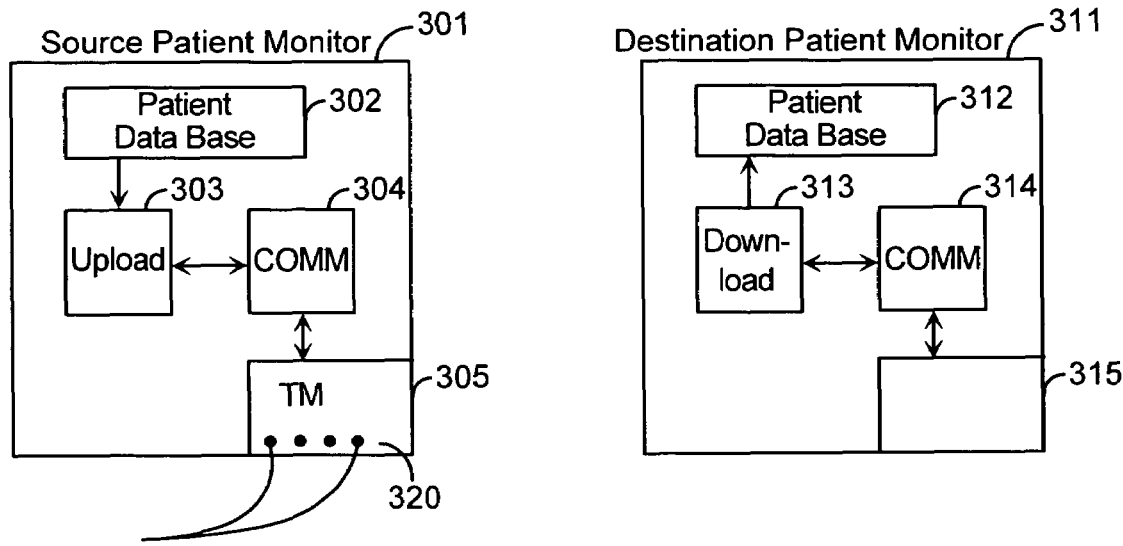
FIG. 3 is a block diagram of a source patient monitor, a destination patient monitor, and a transport module.

FIG. 3 is a block diagram of a source patient monitor, a destination patient monitor, and a transport module. The source patient monitor 301 includes a patient database 302, an upload program 303, a communications program 304, and a transport module connector 305. As shown in FIG. 3, transport module 320 is connected to the source patient monitor 301 through the transport module connector 305. The destination patient monitor 311 includes a patient database 312, a download program 313, a communications program 314, and a transport module connector 315. To transport a patient, a health care provider directs the upload program 303 to extract patient information from the patient database 302 and transfer the extracted information to the transport module 320 through the communications program 304. The transport module 320 is then disconnected from the transport module connector 305. The patient is then transported along with the transport module 320 to a destination location. At the destination location, the health care provider connects the transport module 320 to the destination monitor 311 through the transport module connector 315. The health care provider then directs the download program 313 to transfer patient information from the transport module 320 and store the patient information in the patient database 312. Alternatively, the transport module is connected to a portable monitor for transport to the destination location. At the destination location, the transport module is disconnected from the portable monitor and connected to the destination monitor.

Figure 4:
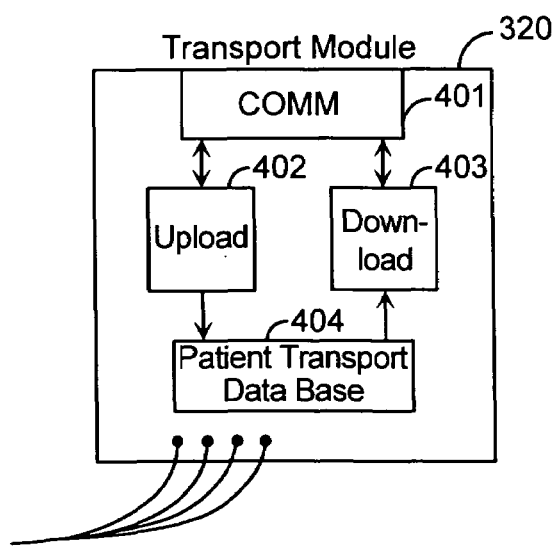
FIG. 4 is a block diagram of a transport module.

FIG. 4 is a block diagram of a transport module. The transport module 320 includes a communications program 401, an upload program 402, a download program 403, and a patient transport database 404. The transport module 320 also includes a sensor interface (not shown) and a program (not shown) for transferring collected data through the communications program 401 to a patient monitor. When information is being uploaded to the transport module 320, the upload program 402 receives the information from the communications program 401 and stores the information in the patient transport database 404. When the transport module 320 receives a request to download information, the download program 403 retrieves information from the patient transport database 304 and sends the information to the communications program 401.

Figure 5:
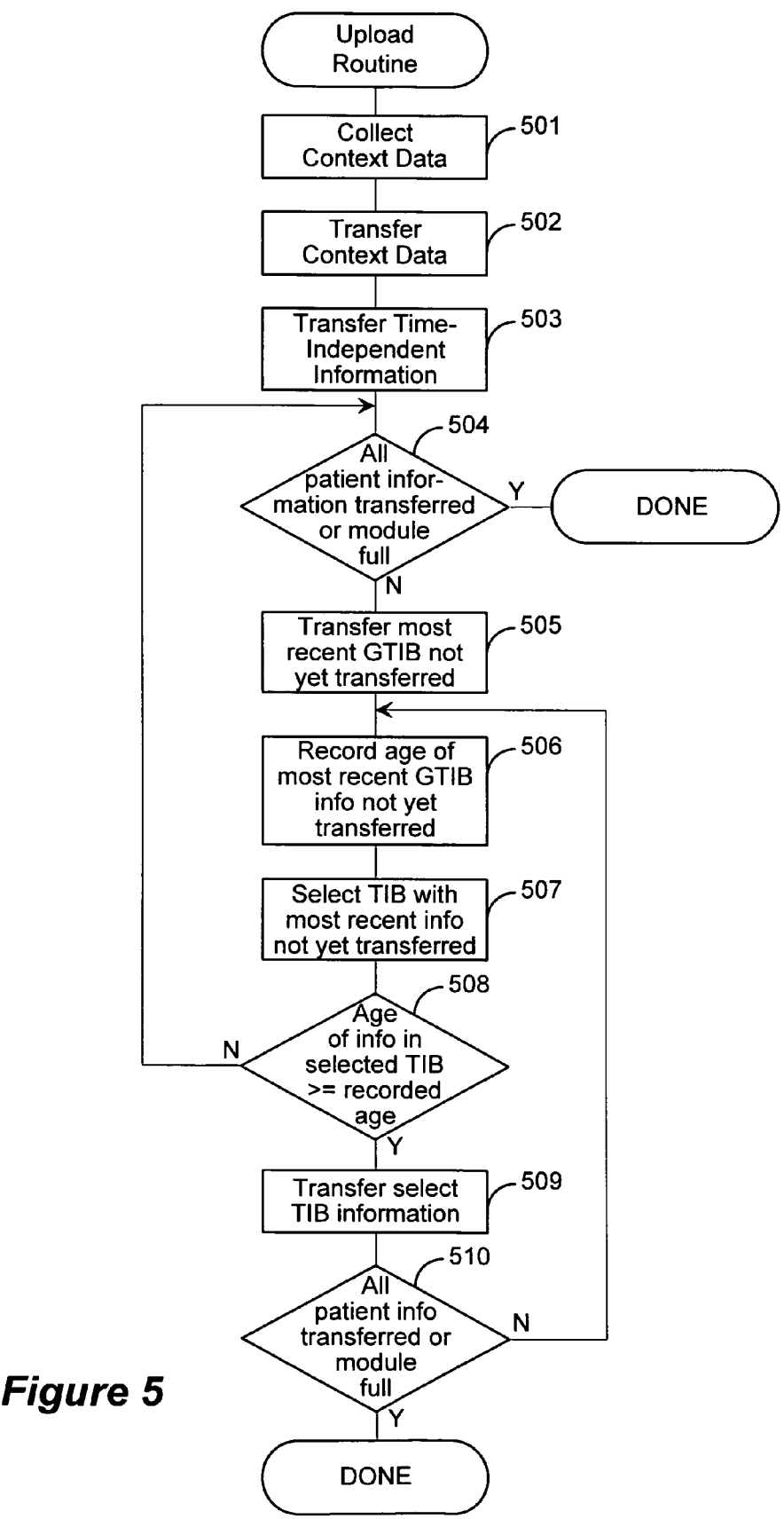
FIG. 5 is a flow diagram of a preferred upload routine of a source patient monitor.

FIG. 5 is a flow diagram of a preferred upload routine of a source patient monitor. The upload routine is executed by the upload program 303 of the source patient monitor. The upload routine transfers information in a way that allows the continued collecting of patient information and storing of the collected information in the patient database 302 and retrieving of the newly collected patient information by a central monitor. The routine first saves a snapshot of the state of the patient database 302 (context data). Once the context data is saved, new patient information can be stored in and retrieved from the patient database 302. The routine uploads the patient information based on the context data. To ensure that time-dependent information is uploaded to reduce the deviations in the currency of the information transferred, the upload routine selects the trend information block with the most recent information that has not yet been transferred and transfers information from the selected block to the transfer buffer and then to the transport module 320. In step 501, the routine saves the context data. The context data is a snapshot of the state of the patient database at the time the upload request is received. The context data includes the next entry number, the time history list, the audit log, and sample time of the context data. In step 502, the routine transfers the context data to the transport module. In step 503, the system transfers time-independent data to the transport module. The time independent data includes a patient descriptive information. In an alternate embodiment, the patient descriptive data is stored as the most-recent general information so that it is transferred first as part of the general information. In step 504, if all the patient information has been transferred or the transport module is full, then the uploading is done, else the routine continues at step 505. In step 505, the routine fills the transfer buffer with the most recent data from the general trend information block not yet transferred and transfers the transfer buffer to the transport module. Before each trend information block is transferred, the system transfers information describing the current state of the trend. This allows trend information to be collected during transfer and reflected in the transferred information until the first block of the trend is transferred. In step 506, the routine records the age of the most current information not yet transferred from the general trend information block. This age is used to determine when the next information from the general trend information block should be transferred. In step 507, the routine selects a trend information block with the most recent information not yet transferred. In step 508, if the age of the most recent information not yet transferred of the selected trend information block is greater than the age of the most recent information not yet transferred from the general trend information block, then the routine continues at step 509, else the routine loops to transfer information from the general trend information block at step 504. In step 509, the routine loads the transfer buffer with information from the selected trend information block and transfers a transfer buffer to the transport module. In step 509, if the transport module is full or all the patient information has been transferred, then the upload routine is complete, else the routine loops to step 507 to select the next trend information block.

Figure 6:
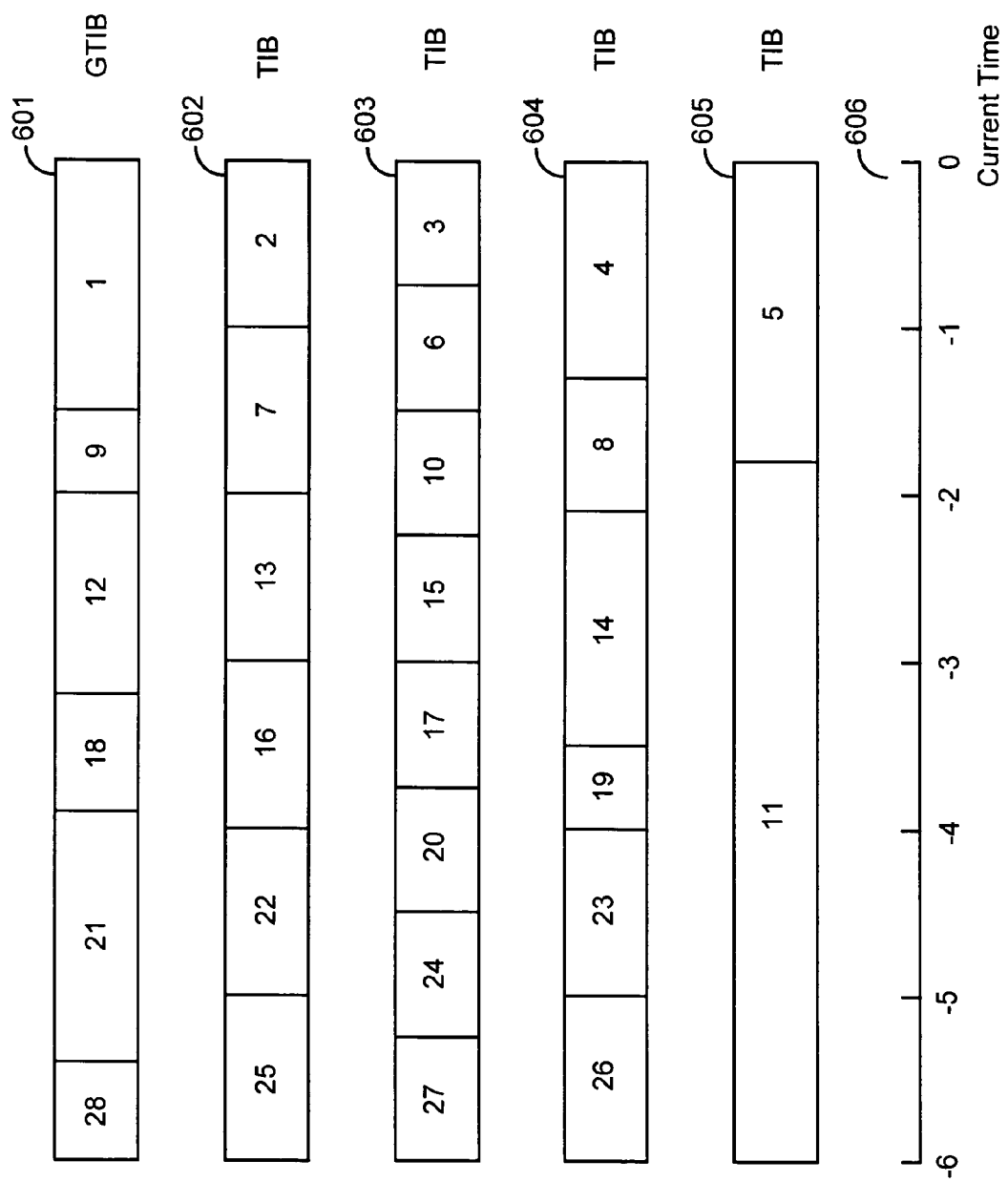
FIG. 6 is a diagram illustrating the ordering of the transferring of information from the trend information blocks to the transport module.

FIG. 6 is a diagram illustrating the ordering of the transferring of information from the trend information blocks to the transport module. Block 601 represents the general trend information block, blocks 603 through 605 represent trend information blocks and timeline 606 indicates the time that entries were added to the trend information blocks. Each block contains transfer blocks. For example, block 601 contains transfer blocks numbered 1, 9, 18, 21, and 28. Each transfer block represents an amount of information (i.e. number of bytes) that will fill the transfer buffer. The time period that the information in a transfer block spans can vary between trend information blocks and can even vary within a trend information block. For example, transfer block 2 corresponds to information spanning one time unit (e.g., one minute) and transfer block 11 corresponds to information spanning over four time units. Nevertheless, the information transfer blocks 2 and 11 each represent one transfer buffer of information.

The numbering of the transfer blocks of FIG. 6 represent the order in which the transfer blocks are transferred to the transport module when uploading. Transfer block 1 corresponds to one transfer buffer of information and is transferred first. Transfer blocks 2, 3, 4, and 5 each represent one transfer buffer of information and are transferred next. Since trend information block 603 contains the most recent information not yet transferred, transfer block 6 is then transferred. Transfer blocks 7 through 28 are then transferred in sequence.

When a transport module uploaded with patient information is loaded into a destination patient monitor, the patient information is downloaded to the patient database. The patient information is preferably downloaded in the same order as it was uploaded. Before downloading the patient information, the transport module transfers the elapsed time since the upload started and a time corresponding to the current time maintained by the source patient monitor. The destination patient monitor stores an entry in the time history list of the patient database indicating a gap in time and to reflect differences in the time maintained by the source and destination patient monitors. The first information received contains the next entry number, the audit log, and the time history list. Once this information is stored in the patient database, the destination patient monitor can collect current patient information while trend information is being downloaded from the transport module.

In an alternate embodiment, when a transport module uploaded with patient information is connected to a destination patient monitor, the downloading of patient information into the patient database may be optionally deferred. The downloading may be deferred when, for example, the patient database of the destination monitor contains information for a patient other than the patient connected to the transport module. When the downloading of patient information is deferred, the destination patient monitor allocates a temporary patient database for the transport module. The transport module once loaded can store information that it collects into the temporary patient database so that the loss of patient information can be minimized. At a later time, a care provider can elect to download the patient information from the transport module or discard the patient information. If the care provider elects to download the patient information, then the downloaded patient information replaces the patient information in the patient database of the destination monitor and then the patient information of the temporary database is merged with patient database. If, however, the care provider elects to discard the patient information of the transport module, then the patient information of the temporary database is merged with the patient database of the destination monitor.

Although the present invention has been described in terms of a preferred embodiment, it is not intended that the invention be limited to this embodiment. Modifications within the spirit of the invention will be apparent to those skilled in the art. The scope of the present invention is defined by the claims that follow.

The invention claimed is:

1. A method for transferring patient information from a source patient monitor having a source patient database to a destination patient monitor having a destination patient database through a transport module, the transport module being connectable to the source patient monitor and destination patient monitor, the transport module having sensors that are connectable to a patient for receiving patient information, the transport module having a transport database for storing patient information, the method comprising the steps of:
  connecting the transport module to the patient;
  connecting the transport module to the source patient monitor;
  receiving an indication that the patient is to be transported;
  in response to receiving the indication that the patient is to be transported, uploading patient information from the source patient database to the transport database of the connected transport module;
  disconnecting the transport module from the source patient monitor;
  transporting the transport module to the destination patient monitor while the transport module is still connected to the patient;
  connecting the transport module to the destination patient monitor; and
  downloading the patient information from the transport database of the connected transport module to thee destination patient database.

2. The method of claim 1 wherein the transport module is disconnected from the source patient monitor and the transport module is connected to the destination patient monitor without disconnecting the transport module from the patient.

3. The method of claim 1 includes the steps of:
  determining a period of time between start of uploading and start of downloading of the patient information; and
  downloading the determined period of time to the destination patient monitor.

4. The method of claim 3 including the step of downloading a time indicative of the start of the uploading of patient information from the transport module to the destination patient monitor.

5. The method of claim 1 wherein the patient information includes a plurality of information streams, each information stream having a plurality of time-ordered entries and wherein the step of uploading includes the steps of:
  selecting an information stream with an entry that has not been uploaded to the transport database and that has the most-recent time-ordering; and
  transferring information from the selected information stream to the transport database.

6. The method of claim 5 wherein the step of uploading includes the step of transferring context data for an information stream to the transport database before transferring information from the information stream to the transport module.

7. The method of claim 6 including the steps of timing an elapsed time period from the uploading of the patient information to the downloading of the patient information and transferring the elapsed time period to the destination patient monitor.

8. The method of claim 1, 2, 3, 4, 5, 6, or 7 wherein the steps of uploading and downloading patient information include the step of allowing concurrent read/write access to the database.

9. A method for downloading patient information stored in a transport patient database on a transport module to a destination patient monitor having a destination patient database, the transport patient database having patient information uploaded from a source patient monitor, the destination patient database having a time history list for tracking adjustments of time and a next entry number for tracking entries added to the destination patient database, the method comprising the steps of:
  connecting the transport module to the destination patient monitor, the transport module being continuously connected to patient during transport of a patient from the source patient monitor to the destination patient monitor;
  sending from the transport module to the destination patient monitor a signal indicative of time since start of upload from the patient source monitor;
  updating the time history list based on the sent signal;
  sending from the transport module to the destination patient monitor a next entry number;
  collecting patient information and storing the collected patient information in the destination patient database identified based on the sent next entry number; and
  transferring patient information from the transport patient database to the destination patient monitor and storing the transferred patient information in the destination patient database.

10. The method of claim 9 wherein the step of transferring patient information from the transport patient database to the destination patient monitor transfers the patient information in the same order as the patient information was uploaded from the source patient monitor.

11. The method of claims 9 or 10 wherein the steps of collecting patient information and transferring patient information occur concurrently.

12. A method of collecting patient information after connecting a transport module containing uploaded patient information to a destination patient monitor having a destination patient database, the method comprising the steps of:

connecting the transport module uploaded with patient information to the destination patient monitor, the transport module being continuously connected to a patient during transport of the patient from a source patient monitor to the destination patient monitor;

allocating a temporary patient database in the destination patient monitor;

collecting patient information;

storing the collected patient information in the temporary patient database; and further comprising:

electing to download the patient information from the transport module to the destination patient monitor;

replacing the destination patient database of the destination patient monitor with the patient information from the transport module; and merging the temporary patient database with the destination patient database of the destination patient monitor.

13. A method of collecting patient information after connecting a transport module containing uploaded patient information to a destination patient monitor having a destination patient database, the method comprising the steps of:

connecting the transport module uploaded with patient information to the destination patient monitor;

allocating a temporary patient database in the destination patient monitor;

collecting patient information;

storing the collected patient information in the temporary patient database; and electing to discard the patient information of the transport module; and merging the temporary patient database with the destination patient database of the destination patient monitor.

* * * * *